US00PP33044P3

(12) United States Plant Patent
Klemm et al.

(10) Patent No.: US PP33,044 P3
(45) Date of Patent: May 11, 2021

(54) ***DIANTHUS* PLANT NAMED 'KLEDG18273'**

(50) Latin Name: ***Dianthus* sp.**
Varietal Denomination: KLEDG18273

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/915,217

(22) Filed: Jun. 29, 2020

(65) Prior Publication Data

US 2021/0037688 P1 Feb. 4, 2021

Related U.S. Application Data

(60) Provisional application No. 62/922,263, filed on Jul. 30, 2019.

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
CPC ..... A01H 6/305
See application file for complete search history.

*Primary Examiner* — Anne Marie Grunberg
(74) *Attorney, Agent, or Firm* — Weatherly IP Solutions, LLC; James Weatherly

(57) ABSTRACT

A new *Dianthus* plant named 'KLEDG18273' particularly distinguished by double flowers with a dark purple color and a magenta flame and a green-grey leaf color, is disclosed.

1 Drawing Sheet

Genus and species: *Dianthus* sp.
Variety denominations: 'KLEDG18273'.

BACKGROUND OF VARIETY 'KLEDG18273'

The present invention comprises a new and distinct variety of *Dianthus*, botanically known as *Dianthus* sp. and hereinafter referred to by the variety name 'KLEDG18273'. 'KLEDG18273' is a selection that resulted from an open pollination of an unnamed and unpatented female *Dianthus* line and an unknown male *Dianthus* line.

In July of 2013, an unnamed female *Dianthus* line and an unknown male *Dianthus* line were cross pollinated in Stuttgart, Germany and seeds were obtained. The seeds were sown and plants were grown for evaluation. A plant line was selected in April of 2014 in Stuttgart, Germany, and named 'KLEDG18273'. In May of 2014, 'KLEDG18273' was first vegetatively propagated by vegetative cuttings. 'KLEDG18273' was found to reproduce true to type in successive generations of asexual propagation via vegetative cuttings in Stuttgart, Germany and Latina, Italy.

SUMMARY OF VARIETY 'KLEDG18273'

The following are the most outstanding and distinguishing characteristics of this new variety when grown under normal horticultural practices in Latina, Italy.

1. Double flowers;
2. A dark purple color with a magenta flame; and
3. A green-grey leaf color.

DESCRIPTION OF THE PHOTOGRAPH

This new *Dianthus* plant is illustrated by the accompanying photograph which show the plant's overall plant habit including form, foliage, and flowers of a 12-week-old plant grown in Stuttgart, Germany under greenhouse conditions in May 2015. The colors shown are as true as can be reasonably obtained by conventional photographic procedures.

DESCRIPTION OF THE NEW VARIETY 'KLEDG18273'

The following detailed descriptions set forth the distinctive characteristics of 'KLEDG18273'. Data was collected on plants potted at eight weeks old in Stuttgart, Germany with the characteristics taken in June of 2019 in Latina, Italy. Color references are to The R.H.S. Colour Chart of The Royal Horticultural Society of London (R.H.S.), 5$^{th}$ edition.

Classification:
- *Family.*—Caryophyllaceae.
- *Species.*—*Dianthus* sp.
- *Common name.*—Pot carnation.
- *Parentage.*—Female: An unnamed and unpatented *Dianthus* line. Male: Unknown *Dianthus*.

Propagation:
- *Type.*—Vegetative cuttings.
- *Time to produce a rooted young plant.*—14 to 18 days.
- *Root description.*—Young roots: RHS 161D. Mature roots: RHS 199C.
- *Rooting habit.*—Lanceolate.

Plant description:
- *Plant form.*—Upright.
- *Plant height.*—17 cm to 21 cm.
- *Plant diameter or spread.*—20 cm to 25.0 cm.

Lateral branches:
- *Length.*—5.0 cm to 10.0 cm.
- *Diameter.*—2.0 cm to 4.0 cm.
- *Internode length.*—2.5 cm to 4.0 cm.

*Number of internodes per branch/stem.*—3 to 5.
*Node length.*—0.2 cm to 0.4 cm.
*Node diameter.*—0.2 cm to 0.4 cm.
*Texture.*—Smooth.
*Color.*—RHS 146C.
*Branch/stem.*—Solid.

Foliage description:
*Arrangement.*—Opposite.
*Length.*—4.0 cm to 7.0 cm.
*Width.*—0.3 cm to 0.5 cm.
*Shape.*—Lanceolate.
*Apex.*—Acute.
*Base.*—Obtuse.
*Margin.*—Entire.
*Texture.*—Upper and lower surfaces: Smooth.
*Venetian pattern.*—None.
*Venetian color.*—None.
*Color.*—Immature and mature leaves: Upper surface: RHS 146B. Lower surface: RHS 146C. Mature leaves: Both surfaces: RHS 191A.

Flower description:
*Flower type and habit.*—Double flower, round.
*Fragrance.*—Present.
*Natural flowering season.*—Spring to fall.
*Position of flowers relative to the foliage.*—Moderately.
*Number of flowers per spray.*—3 to 4.
*Flower longevity on the plant.*—14 to 16 days.
*Flower buds.*—Length: 1.5 cm to 2.0 cm. Diameter: 0.4 cm to 0.6 cm. Shape: Elliptic. Color: RHS 147B. Extrusion of the styles at the bud stage: Absent.
*Corolla.*—Quantity of petals/arrangement: 10 to 14. Corolla height: 0.8 cm to 1.5 cm. Petal length: 3.0 cm to 3.5 cm. Petal width: 1.2 cm to 1.6 cm. Petal shape: Spoon shaped. Petal apex: Obtuse. Petal base: Acute. Petal margin: Serrated. Depth of petal margin: Medium. Petal texture:. Upper and lower surfaces: Smooth. Petal color: Immature: Upper surface: RHS 79A and flamed RHS 80B. Lower surface: RHS 80D and outer border RHS 80B. Mature: Upper surface: RHS 79A and flamed RHS 80B. Lower surface: RHS 80D and outer border RHS 80B. Calyx: Quantity of sepals/arrangement: Composed of 5 sepals. Shape: Campanulate. Calyx height: 1.5 cm to 2.0 cm. Calyx diameter, at the apex: 0.3 cm to 0.5 cm. Sepal texture: Upper and lower surfaces: Smooth. Sepal color: Upper surface: RHS 137A. Lower surface: RHS 137D.

Peduncles:
*Length.*—1.0 cm to 2.0 cm (last internode), whole stem 10.0 cm.
*Diameter.*—0.1 cm to 0.2 cm.
*Strength.*—Moderate.
*Texture.*—Smooth.
*Color.*—RHS 191A.

Reproductive organs:
*Stamens.*—Quantity: 4 to 8. Filament length: 1.5 cm to 2.0 cm. Filament color: RHS 157B. Anther length: 0.2 cm to 0.3 cm. Anther diameter: 0.1 cm. Anther color: RHS 85C. Pollen amount: Moderate.
*Pistils.*—Quantity: 2 styles. Pistil length: Not observed. Style length: 1.0 cm to 2.0 cm. Style color: RHS 155D. Stigma shape: Filamentous. Stigma color: RHS 85C. Ovary size: 0.5 cm to 0.7 cm. Ovary shape: Oval. Ovary color: RHS 145C. Fruits/seeds: Seed sometimes observed.

Disease and insect/pest resistance: No special observations were made.

COMPARISON OF 'KLEDG18273' WITH KNOWN VARIETY

When 'KLEDG18273' is compared to the commercial line 'KLEDG18305' (U.S. patent application Ser. No. 15/998,600), the following differences are noted in Table 1:

TABLE 1

Comparison with Similar Variety

| Trait | Variety 'KLEDG18273' | Commercial line 'KLEDG18305' |
|---|---|---|
| Flower type | Double | Single |
| Flower color | Dark purple, magenta flamed | Pink with purple ring |
| Leaf color | Green-grey | Dark green |

We claim:

1. A new and distinct variety of *Dianthus* plant named 'KLEDG18273' as shown and described herein.

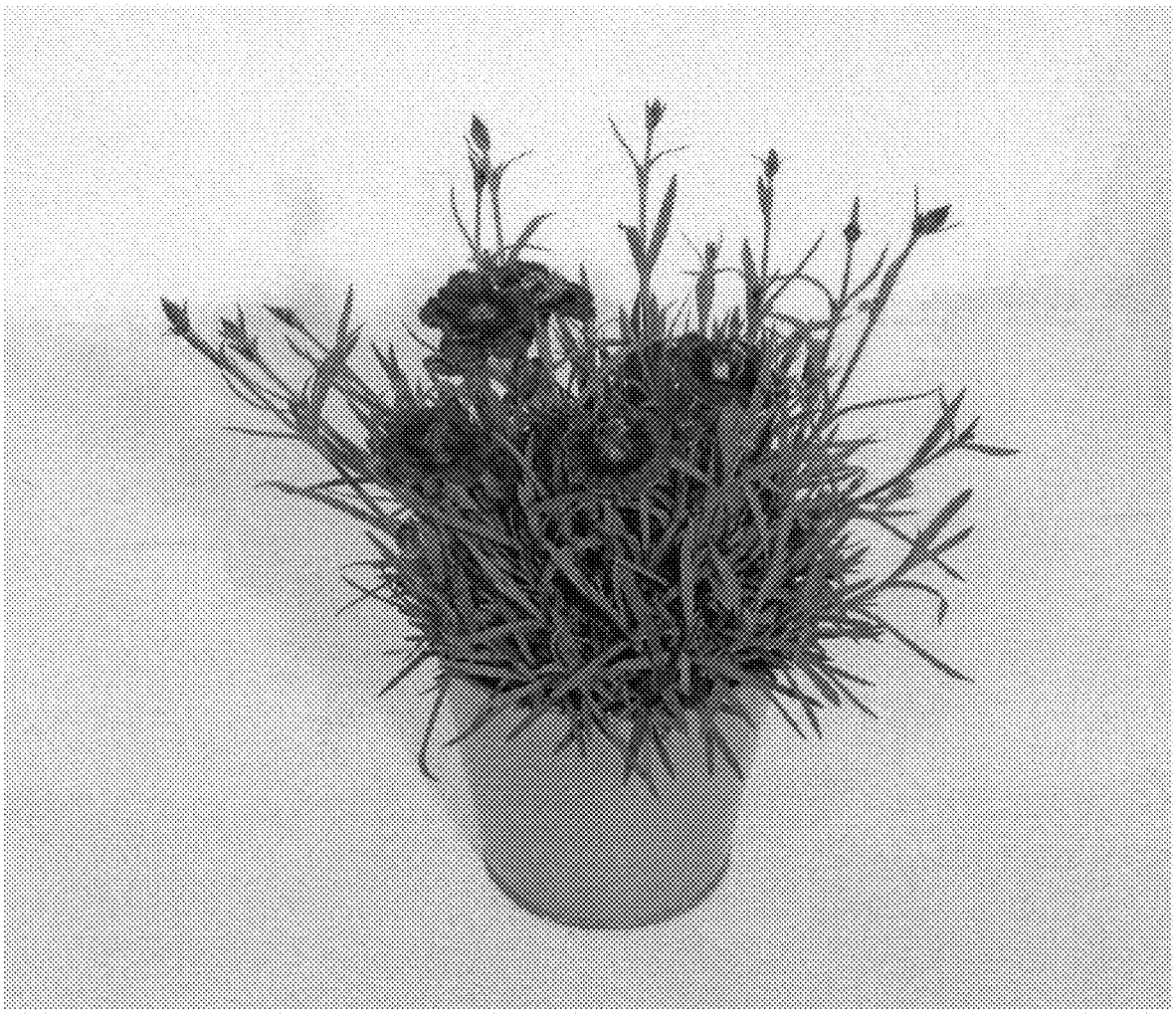

* * * * *